US00PP26747P2

(12) United States Plant Patent
Kordes

(10) Patent No.: US PP26,747 P2
(45) Date of Patent: May 24, 2016

(54) HYBRID TEA ROSE PLANT NAMED 'KORBERONEM'

(50) Latin Name: *Rosa hybrida*
Varietal Denomination: KORberonem

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 112 days.

(21) Appl. No.: 14/121,044

(22) Filed: Jul. 23, 2014

(51) Int. Cl.
*A01H 5/02* (2006.01)

(52) U.S. Cl.
USPC ..... Plt./130

(58) Field of Classification Search
USPC ..... Plt./136, 130
See application file for complete search history.

(56) References Cited

PUBLICATIONS

HelpMeFind www.helpmefind.com/rose/pl/php?n=94484, pulled from the Internet Jan. 6, 2016.*
HelpMeFindKordes & Sons (https://www.helpmefind.com/gardening/l.php?l=7.5937), pulled from the Internet Jan. 8, 2016.*

* cited by examiner

*Primary Examiner* — Anne Grunberg

(57) ABSTRACT

A new and distinct variety of rose with long lasting, novel cream-apricot colored flowers, and attractive foliage with very good disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORberonem'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2004. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORberonem'.

SUMMARY OF THE INVENTION

The new rose plant may be distinguished from its seed parent, an un-named seedling, by the following combination of characteristics:

1. 'KORberonem' has cream-apricot colored flowers, whereas the un-named seedling has yellow flowers.
2. 'KORberonem' has medium-sized flowers, whereas the un-named seedling has very large flowers.

The new rose plant may be distinguished from its pollen parent, an un-named seedling, by the following combination of characteristics:

1. 'KORberonem' has cream-apricot colored flowers, whereas the un-named seedling has yellow flowers.
2. 'KORberonem' has a double petal count, whereas the un-named seedling has a semi-double petal count.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORberonem' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORberonem' was selected in May 2005 from the seedling beds to be asexually propagated for further evaluation. The first asexual propagation of 'KORberonem' was done by budding in July 2005 at the inventor's nursery in Offenseth-Sparrieshoop, Germany.

These initial and other subsequent propagations conducted in controlled environments demonstrate that 'KORberonem' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORberonem'.

DETAILED BOTANICAL DESCRIPTION

The following is a description of 'KORberonem', as observed growing in June 2014 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORpenparo', a rose variety from the same inventor described and illustrated in U.S. Plant Pat. No. 21,471 issued on Nov. 16, 2010 are compared to 'KORberonem' in Chart 1.

CHART 1

| Characteristic | 'KORberonem' | 'KORpenparo' |
|---|---|---|
| Diameter of open flower. | 75 mm. | 90-110 mm. |
| General tonality on open flower. | Red Group 36D. | Yellow-White Group 158B. |
| Leaf size. | 150 to 170 mm (l) × 115 to 135 mm (w). | 60 mm (l) × 110 mm (w). |

Parents:

*Seed parent*.—An un-named seedling.

*Pollen parent*.—An un-named seedling.

Classification:

*Botanical classification*.—*Rosa hybrida* 'KORberonem'.

*Commercial classification*.—Hybrid tea rose.

FLOWER AND FLOWER BUD

Blooming habit: Recurrent. Floriferous.

Flower bud:

*Size*.—Upon opening, 33 mm in length from base of receptacle to distal end of bud and 40 mm diameter at its widest point.

*Bud form*.—Globular.

*Bud color*.—As sepals first unfold, bud color is Yellow-Green 154D with intonations of Greyed-Purple 184D. When ¼ open, the upper surface of petals is Yellow Group 2D in the basal zone and White Group 155D in the middle and marginal zones, with intonations of Red Group 38D on the margins. The lower surface is Yellow Group 2D in the basal zone and White Group 155B in the middle and marginal zones, with intonations of Red Group 38B at the margins. Outermost petals are Green-Yellow Group 1D in the basal zone, Green-White Group 157C in the middle and marginal zones, with intonations of Red-Purple Group 60A along the midrib and Yellow-Green Group 145C on the margins.

*Sepals*.—Color: Upper surface: Yellow-Green Group 145B. Lower surface: Yellow-Green Group 144C. Size: Average 25 mm (l)×10 mm (w). Shape: Moderate foliaceous appendages on 3 of the five sepals. Apex: Apiculate. Base: Flat at union with receptacle. Quantity: Five. Surface texture: Upper side: Silky and strongly pubescent. Lower surface: Leathery and lightly pubescent. Margins: Cilliate to pectinate. Stipitate glands: Abundant on margins and lower surface.

Flower bloom:

*Fragrance*.—Strong anise fragrance.

*Duration*.—On the plant 5 days. Senesced petals drop away cleanly.

*Size*.—Medium for a hybrid tea rose. When open, the average flower diameter is 75 mm and the average flower height is 35 mm.

*Form*.—Shape of flower when viewed from the side: Upon opening, upper part: Flat. Upon opening, lower part: Concave. Open flower, upper part: Flat. Open flower, lower part: Concave.

Color:

*Upon opening, petals*.—Outermost petals: Outer Side: Yellow Group 2D in the basal zone, and White Group 155B in the middle and marginal zones, with intonations of Red-Purple Group 58D on the margins. Inner Side: Yellow Group 2D in the basal zone, and White Group 155A in the middle and marginal zones, with intonations of Red-Purple Group 58D on the margins. Innermost petals: Outer Side: White Group 155D in the basal and middle zones, and White Group N155B in the marginal zone. Inner Side: White Group 155B in the basal and middle zones, and White Group N155B in the marginal zone.

*Upon opening, basal petal spots*.—Basal petal spot, outermost petals: None observed. Basal petal spot, innermost petals: Outer Side: Yellow Group 3C. Inner Side: Yellow Group 3C.

*After opening, petals*.—Outermost petals: Outer Side: Yellow Group 2D in the basal zone, and Orange-White Group 159C in the middle and marginal zones, with intonations of Red Group 38C on the margins. Inner Side: Yellow Group 2D in the basal zone, and Orange-White Group 159C in the middle and marginal zones, with intonations of Red Group 38C on the margins. Innermost petals: Outer Side: White Group 155A in the basal zone, White Group N155D in the middle zone, and White Group N155C in the marginal zone. Inner Side: White Group 155A in the basal zone, White Group N155D in the middle zone, and White Group N155C in the marginal zone.

*After opening, basal petal spots*.—Basal petal spot, outermost petals: Outer Side: None observed. Inner Side: Yellow Group 3B. Basal petal spot, innermost petals: Outer Side: Yellow Group 3C. Inner Side: Yellow Group 3B.

General tonality: On open flower Red Group 36D. No change in the general tonality at the end of the 4 day. Afterwards, general tonality is White Group N155D.

Petals:

*Petal count*.—Double.

*Average range*.—Approximately 30 to 35 petals under normal conditions.

*Petal reflex*.—Petals reflex strongly.

*Petal margin*.—Typically entire, occasionally ruffled on innermost petlas.
*Petal shape*.—Obovate. Apex: Obtuse. Base: Cuneate.
*Petal size*.—30 to 40 mm (l)×30 to 40 mm (w).
*Petal arrangement*.—Formal.
*Texture*.—Smooth.

Petaloids:
*Petaloid count*.—Average of 12 per flower.
*Petaloid size*.—Variable. 10 to 25 mm (l)×6 to 10 mm (w).
*Petaloid color*.—Inner side: Yellow Group 2D in the basal zone, Red Group 36D in the middle zone, and Red Group 36A in the marginal zone. Outer side: Yellow Group 2D in the basal zone, Red Group 36D in the middle zone, and Red Group 36A in the marginal zone.
*Petaloid texture*.—Smooth.
*Margins*.—Variable. Most commonly undulated and indented.
*Petaloid shape*.—Most commonly spatulate and oblong, with some petaloids highly irregular. Apex: Acute. Base: Cuneate to attenuate.

Reproductive organs:
*Pistils*.—Abundant. Approximately 100 present. Stigmas: Location: Inferior in position to anthers. Color: Greyed-Yellow Group 160A. Styles: Length: About 3 to 4 mm long. Color: Red Group 51A.
*Stamens*.—Approximately 120 on average and regularly arranged. Anthers: Size: Average 2 mm (l)×1 mm (w). Pollen: Generally present. Color: Yellow-Orange Group 17A. Filaments: Color: Yellow Group 3B. Length: 5 to 12 mm.

Receptacle:
*Surface*.—Generally glabrous, with limited numbers of fine hairs.
*Color*.—Yellow Green Group 144A with intonations of Greyed-Purple Group 187A and 187B.
*Shape*.—Urn-shaped.
*Texture*.—Smooth.
*Size*.—7 to 10 mm (h)×10 to 12 mm (w).

Pedicel:
*Surface*.—Abundant stipitate glands and limited numbers of fine hairs.
*Length*.—60 mm average length.
*Diameter*.—3 mm average diameter.
*Color*.—Yellow-Green Group 145A with intonations of Greyed-Purple Group 184C.
*Strength*.—Strong.
*Texture*.—Papillate.
*Borne*.—Multiple flower buds per stem, generally 1 to 6. Flowers held upright.

Peduncle:
*Surface*.—Glabrous.
*Length*.—65 mm average length.
*Diameter*.—4 mm average diameter.
*Color*.—Yellow-Green Group 146C with intonations of Greyed-Purple Group 184B and 184C.
*Strength*.—Strong.
*Borne*.—Multiple flower buds per stem, generally 1 to 6.

THE PLANT

Growth: Vigorous growth.

Plant habit: Upright. When grown as a field plant, the average plant height is 120 cm and the average plant width is 50 cm.

Stems:
*Stem color*.—Young wood: Yellow-Green Group 145A. Older wood: Yellow-Green Group 144A.
*Intonations*.—Greyed-Purple Group 184B, present on young wood.
*Stem surface texture*.—Young wood: Smooth. Older wood: Smooth.

Prickles: Present.
*Incidence*.—Average of 5 per each 10 cm of stem.
*Size*.—Average length: 10 mm.
*Color*.—Immature prickles: Yellow-Green Group 145C. Mature prickles: Yellow-Green Group 145C. Senescing to Grey-Brown Group 199B.
*Shape*.—Concave.
*Anthocyanin*.—Color: Greyed-Purple Group 184C on most prickles.

Leaves: Normally 7 leaflets on normal leaves in middle of the stem.
*Venation pattern*.—Pyramidal net pattern.
*Leaf size*.—150 to 170 mm (l)×115 to 135 mm (w).
*Abundance*.—Very abundant.

Leaflets:
*Size*.—Average size of the terminal leaflet is 70 to 75 mm (l)×50 to 55 mm (w).
*Shape*.—Elliptic. Base: Obtuse. Apex: Acute to cuspidate.
*Margins*.—Serrated.
*Surface*.—Semi-glossy.
*Texture*.—Upper side of leaflet: Smooth. Under side of leaflet: Rugose.
*Color, mature foliage*.—Upper Leaflet Surface: Yellow-Green Group 147A. Lower Leaflet Surface: Yellow-Green Group 146B.
*Color, juvenile foliage*.—Upper Leaflet Surface: Yellow-Green Group 144A. Lower Leaflet Surface: Yellow Green Group 146C and 146D.
*Anthocyanin intonation*.—Greyed-Purple 184B. Location: Present on juvenile foliage, most commonly on margins.
*Arrangement*.—Odd pinnate.
*Venation*.—Reticulate.

Stipules:
*Size*.—22 mm (l)×7 mm (w).
*Stipule color*.—Yellow-Green Group 144B.
*Anthocyanin*.—Greyed-Purple Group 184D.
*Stipitate glands*.—Limited numbers on margins.
*Margins*.—Cilliate.
*Texture*.—Smooth.
*Shape*.—Apex: Apiculate. Base: Winged.

Petiole:
*Length*.—Average 27 mm.
*Diameter*.—Average 2 mm.
*Petiole color*.—Yellow-Green Group 146B. Underneath: Yellow-Green Group 146D.
*Margins*.—Cilliate.
*Anthocyanin*.—Limited intonations on midrib and prickles of Greyed-Purple Group 184D.
*Prickles*.—A few small prickles underneath.
*Stipitate glands*.—Limited numbers present on margins.
*Texture*.—Pubescent.

Petiole rachis:
*Length*.—Average 20 mm.
*Diameter*.—Average 2 mm.

*Color*.—Yellow-Green Group 146C. Anthocyanin: Limited intonations of Greyed-Purple 184C on midrib and prickles of juvenile tissue.

*Margins*.—Cilliate.

*Prickles*.—A few small prickles underneath.

*Stipitate glands*.—Very few present on margins.

Hips/seed formation: None observed.

Winter hardiness: To date, the variety has been grown successfully in Zone 5.

Disease resistance: Very good resistance to powdery mildew (*Sphaerotheca pannosa*), and blackspot (*Diplocarpon rosae*) diseases under normal growing conditions in Jackson County, Oreg.

I claim:

1. A new and distinct variety of rose plant, as described and illustrated herein.

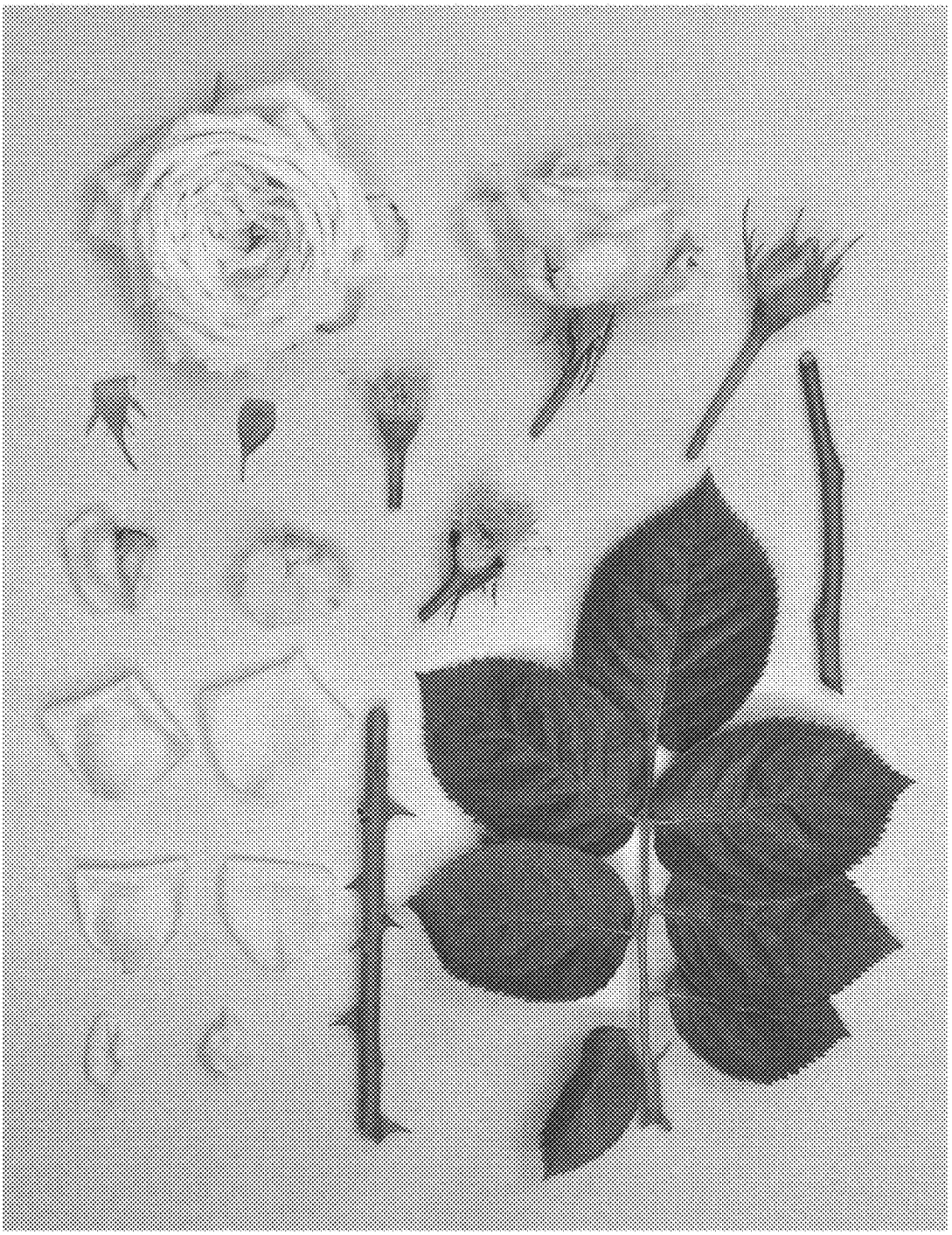

* * * * *